(12) United States Patent
Brocia

(10) Patent No.: US 7,279,297 B2
(45) Date of Patent: Oct. 9, 2007

(54) EX VIVO METHOD FOR DETERMINATION OF CETP ACTIVITY AND EFFICACY OF HEART DISEASE TREATMENT

(75) Inventor: Robert W. Brocia, Bronxville, NY (US)

(73) Assignee: Roar Holding LLC, New York, NY (US)

( * ) Notice: Subject to any disclaimer, the term of this patent is extended or adjusted under 35 U.S.C. 154(b) by 297 days.

(21) Appl. No.: 10/413,419

(22) Filed: Apr. 11, 2003

(65) Prior Publication Data

US 2004/0018578 A1    Jan. 29, 2004

Related U.S. Application Data

(60) Provisional application No. 60/372,628, filed on Apr. 11, 2002.

(51) Int. Cl.
*C12Q 1/48*    (2006.01)
(52) U.S. Cl. ....................................................... 435/15
(58) Field of Classification Search ................... None
See application file for complete search history.

(56) References Cited

U.S. PATENT DOCUMENTS

| 5,512,548 A |   | 4/1996  | Kushwaha et al. ............. 514/12  |
|-------------|---|---------|--------------------------------------|
| 5,585,235 A |   | 12/1996 | Brocia ............................ 435/4 |
| 5,618,683 A |   | 4/1997  | Brocia et al. ................... 435/11 |
| 5,770,355 A | * | 6/1998  | Brocia ............................ 435/4 |
| 6,174,693 B1|   | 1/2001  | Brocia .......................... 435/7.4 |
| 6,313,142 B1|   | 11/2001 | Damon et al. ................. 514/313 |

FOREIGN PATENT DOCUMENTS

WO    WO-94/24567    10/1994

OTHER PUBLICATIONS

CARDIOCHEK Microwell ELISA Assays Product Insert accessed Sep. 1, 2005 http://nlbbs.com/~alerchek/coronaryArteryDisease.htm.*
Bisgaier, C. et al., "Use of Fluorescent Cholesteryl Ester Microemulsions in Cholesteryl Ester Transfer Protein Assays" Journal of Lipid Research 34:1625-1634 (1993).
Dousset, N. and Douste-Blazy, L., "Fluorescent Determination of Cholesteryl Ester Transfer Protein (CETP) Activity in Plasma" Clinical Chemistry 38(2):306 (1982).
Epps, D. et al., "Method for Measuring the Activities of Cholesteryl Ester Transfer Protein (Lipid Transfer Protein)" Chemistry and Physics of Lipids 77:51-63 (1995).
Milner, T. et al., "Enhancement of the Human Plasma Lipid Transfer Protein Reaction by Apolipoproteins" Biochimica Biophysica Acta 1082:71-78 (1991).
Nichols, A. and Smith, L. "Effect of Very Low-Density Lipoproteins on Lipid Transfer in Incubated Serum" Lipid Research 6:206-210 (1965).
Pattnaik, N. et al., "Cholesteryl Ester Exchange Protein in Human Plasma Islolation and Characterization" Biochemica et Biophysica Acta 530:428-438 (1978).
Hayashibe, et al. (1997) *Atherosclerosis* 129:53-58.
Serdyuk, et al. (1999) *Arterioscler Thromb Vasc Biol* 19(3):718-726.
Supplementary European Search Report for EP 03724023.1, mailed on Sep. 8, 2006, 3 pages.

* cited by examiner

*Primary Examiner*—Jon Weber
*Assistant Examiner*—Paul Martin
(74) *Attorney, Agent, or Firm*—Morrison & Foerster LLP

(57) ABSTRACT

The present invention relates to a novel method to determine CETP activity in a bodily fluid sample wherein the sample may contain an inhibitor of CETP activity. The effect of the inhibitor is preserved to provide a more accurate determination of CETP activity in the fluid. Kits for the practice of the method are also provided.

16 Claims, 4 Drawing Sheets mAb (µl stock in 2 µl total volume) / 50 µl plasma

GRAPH 1

EX VIVO METHOD FOR DETERMINATION OF CETP ACTIVITY AND EFFICACY OF HEART DISEASE TREATMENT

CROSS-REFERENCE TO RELATED APPLICATIONS

This application claims priority under 35 U.S.C. § 119(e) to provisional application 60/372,628, filed 11 Apr. 2002, which is hereby incorporated by reference as if fully set forth.

TECHNICAL FIELD

This invention relates generally to methods of determining Cholesteryl Enzyme Transfer Protein (CETP) activity in bodily fluids of a subject with increased accuracy by reducing undesirable dilution effects present in other assays for CETP activity. The methods are applied in the form of heart disease test kits and methods of determining heart disease risk factors as well as methods of determining the efficacy of treatments for heart disease. The present invention also relates to a method and kit for determining an atherosclerosis risk factor as well as methods and kits for determining the efficacy of a treatment regimen for abnormalities associated with CETP activity.

BACKGROUND ART

It is known that heart disease or atherosclerosis is a result of the build up and subsequent restriction of blood vessels by plaque of circulating blood to the heart muscle. It is believed a preemptive factor to plaque development is depositing or loading of the cells comprising the blood vessel lining with cholesterol in the form of cholesteryl ester. It is also believed the cholesteryl ester originates from sources that include lipoproteins, specifically the low density (LDL) and very low density (VLDL) lipoproteins. The high density lipoproteins (HDL), however, are known to be protective elements where heart disease or atherosclerosis is concerned and are desirable lipoproteins.

The medical profession utilizes several methods to minimize the exposure of cells that line the circulatory system to VLDL and LDL with the rationale that lowering the exposure of arterial walls to LDL and VLDL will lower the ability of the cells to load or uptake cholesteryl ester from these lipoproteins. Means of lowering LDL and VLDL include indirect means such as disruption of the cholesterol biosynthetic pathway that occurs within the liver cells. Drugs, such as the statins, including Mevacor® and Lipitor® inhibit HMG-Coenzyme A reductase, a key enzyme along the cellular pathway for production of cholesterol.

Cholesterol is a life sustaining component necessary to maintain many basic functions such as cell membrane integrity. Cholesterol is transported throughout the circulatory system within lipoproteins in the ester form as cholesteryl ester. The ester is completely water insoluble and resides in the core of the lipoproteins. Statin drugs are given in limited doses so that the pathway is not totally without output of cholesterol but the output is partially reduced. The reduced cholesterol output from the liver results in generally a reduction of all cholesterol pools or stores. Included is the reduction of the lipoprotein cholesterol pool. Lipid transfer proteins or other proteins that utilize lipids as substrates interact with the lipoproteins to access their substrates both at the core and the surface of the lipoprotein. One lipid transfer protein, in particular a neutral lipid transfer protein, cholesteryl ester transfer protein (CETP), which shuttles cholesteryl esters from HDL to VLDL and LDL.

There are various known techniques to measure cholesteryl ester transfer protein (CETP) activity. For example, an article entitled: Effect of Very Low-Density Lipoproteins on Lipid Transfer in Incubated Serum, by A. V. Nichols and L. Smith, J. Lipid Research, vol. 6, pp. 206-210 (1965), measures the activity of CETP by determination of cholesteryl ester (CE) mass transfer. The determination of CE mass transfer from high density lipoprotein to very-low density lipoprotein (VLDL) and low density lipoprotein (LDL) requires the re-isolation of VLDL and LDL after incubation with HDL and the CETP source in order to determine the cholesteryl ester mass transfer.

The VLDL/LDL re-isolation from the incubation mixture is a technique that includes ultra-centrifugation of the incubation mixture for many hours so that the VLDL and LDL components are floated upwards through a density gradient as the HDL component of the incubation mixture sinks to the bottom of the centrifuge tube. Further processing of the sample requires a method of determining the amount or mass of cholesteryl ester associated with the re-isolated VLDL or LDL and equating a change in mass to CETP facilitated transfer. Later variations of this method of activity measurement have simplified mass determination by utilizing HDL that has a radioactive label associated with the CE.

An article entitled: Cholesteryl Ester Exchange Protein in Human Plasma Isolation and Characterization by N. M. Pattnaik, A. Montes, L. B. Hughes and D. B. Zilversmit, Biochemica et Biophysica Acta 530, pp. 428-438 (1978), discloses a method of activity measurement of CETP that also utilizes radioactive CE in HDL. This method is an improvement over the above method by simplifying the incubation mixture components separation or the re-isolation technique discussed above. In the cited article, separation of the LDL component from the HDL component is accomplished by precipitation of the LDL component of the incubation mixture. The LDL precipitate is pelleted by a relatively short slow-speed centrifugation and the remaining HDL supernatant is counted. The loss of radioactivity from the HDL component is attributed to 3H-CE transferred to the LDL pellet.

An article titled: Fluorescent Determination of Cholesteryl Ester Transfer Protein (CETP) Activity in Plasma by N. Dousset, L. Douste-Blazy in Clinical Chemistry, vol. 38, No. 2, p. 306 (1982), is an improvement over previous methods of activity measurement since it discloses a technique that does not require radioactive components. In this method, transfer activity of the CETP is determined by the measurement of transfer of a fluorescent labeled CE. In this reference, the cholesteryl ester molecule utilized as the CETP substrate for transfer has been covalently bound to a fluorescent molecule derived from pyrene. The pyrene labeled cholesteryl ester (PY-CE) is recognized by the CETP and the PY-CE may be detected by a fluorimeter. The accumulation of the PY-CE in the LDL fraction is, however, only able to be determined after the separation of the LDL acceptor from the HDL donor.

An article entitled: Enhancement of The Human Plasma Lipid Transfer Protein Reaction by Apolipoproteins by T. G. Milner, K. W. S. Ko, T. Ohnishi, and S. Yokoyama in Biochimica Biophysica Acta 1082, pp. 71-78 (1991), discloses a method for determining the activity of CETP also utilizing a pyrene labeled CE (PY-CE). This method does not require separation or re-isolation of substrates, but uses the measurement of both monomer and excimer fluorescent emission from the pyrene label to determine a ratio thereof. The cited article improves upon certain aspects of the previous method.

An article entitled: Use of Fluorescent Cholesteryl Ester Microemulsions in Cholesteryl Ester Transfer Protein Assays by Charles L. Bisgaier, Laura Minton, Arnold D. Essenberg, Andrew White, and Reynold Homen published in the Journal of Lipid Research, Volume 34, 1993 discloses a method that utilizes a self-quenching fluorescent labeled cholesteryl ester core.

Additionally, there are methods disclosed by the present inventor in U.S. Pat. Nos. 5,770,355; 5,618,683; 5,585,235 and 6,174,693.

Citation of the above documents is not intended as an admission that any of the foregoing is pertinent prior art. All statements as to the date or representation as to the contents of these documents is based on the information available to the applicant and does not constitute any admission as to the correctness of the dates or contents of these documents.

DISCLOSURE OF THE INVENTION

The invention is directed to assays for CETP activity in bodily fluids of a subject, which methods have improved accuracy. The invention is based in part on the recognition that inhibitors of CETP activity may be present in bodily fluids and that dilution of the bodily fluids in an assay method dilutes such inhibitors to result in an inaccurate assessment of CETP activity in the bodily fluid. Inhibitors of CETP may be present in the bodily fluids of a subject as a result of various factors, including, but not limited to, administration of a CETP inhibitor (or prodrug form thereof) to said subject, endogenous inhibitors that are ordinarily present in said subject, and endogenous inhibitors that are induced by administration of a medication, dietary factors, and/or physical activity. There are reports of endogenous inhibitors of CETP (see for example, U.S. Pat. No. 5,512,548) in addition to chemical inhibitors (see for example, U.S. Pat. No. 6,313,142). Such inhibitors may include apoC-I.

Previous methods fail to allow the measurement of CETP activity in a bodily fluid, such as plasma, when an inhibitor is also present in the fluid at an effective concentration. This failure is because those methods require dilution of the plasma or serum sample in the assay used. This results in the dilution of the inhibitor below the concentration that was originally present in vivo and thus possibly below the concentration where it inhibits CETP. This dilution effect creates a problem in obtaining an accurate determination of CETP activity in the bodily fluid because it is not readily possible to determine the identities, and amounts thereof, of inhibitors present in a sample of bodily fluid from a subject, such as a human patient. The same problem arises whenever a sample of bodily fluid is added to an assay of a volume significantly greater than the sample volume.

The present invention provides an ex vivo assay that does not require significantly alterations in the concentration of a CETP inhibitor that may be present in a bodily fluid sample. Thus more accurate measurements of CETP activity in a bodily fluid sample may be made despite the presence of an inhibitory drug or compound in the sample. Of course the invention may also be practice with samples that are free of exogenously supplied CETP inhibitors to provide a more accurate determination of CETP activity in a bodily fluid.

Thus in one aspect, the present invention provides a method for the determination of CETP activity in a bodily fluid sample, such as a plasma sample, without dilution of the sample in order to make CETP activity measurements in samples that may or may not be treated with CETP inhibitors. In addition to preventing dilution of possible inhibitors of CETP activity, the present invention permits measurement of CETP activity in biological fluids without significant alteration of the concentration of the components of the biological fluid.

In one embodiment, the ex vivo method includes 50 microliters of a bodily fluid, such as a plasma sample, to be assayed and 4 microliters of assay reagents in a homogeneous CETP activity assay. Of course larger and smaller volumes, such as from about 10 to about 100 microliters, of a bodily fluid may be used in the present invention, which provides assay conditions where the physiological sample is present as a majority of the total assay volume. Preferably, the majority is about 90% or greater of the assay volume. These conditions are preferably applied to measure the effect of a drug at a specific concentration in a patient's plasma sample and to collect data regarding the effect of the drug on CETP activity at specific concentrations. The assay reagents comprise a donor particle and an acceptor wherein the donor particle contains a substrate for transfer by CETP. The substrate is preferably labeled such that the transfer of the substrate from the donor particle to an acceptor is detected as an indicator of CETP activity.

Given the role of CETP activity in disorders such as coronary artery lesions and others involving cholesteryl ester deposits, the present invention is preferably applied to solve a variety of problems facing health care providers such as physicians, clinical hospital staff, laboratories, pharmaceutical companies and the like, in the diagnosis of risk factors for heart disease and atherosclerosis. The invention provides hundreds of millions of individuals who are at risk of developing heart disease and atherosclerosis, either as a result of genetic factors, diet, or the like, with a simple diagnostic tool and method for more accurately diagnosing risk factors for these conditions. The invention also provides means to determine the efficacy of treatments of lipid transfer protein disorders and in particular CETP related disorders such as coronary artery lesions. The invention targets this group of hundreds of millions of individuals worldwide by providing a method and kit for determining a heart disease risk factor, namely, abnormal activity of CETP, and a method and kit for determining the efficacy of a treatment that targets CETP activity.

The present invention is preferably embodied as a non-radioactive method and kit to simplify, facilitate the determination of, and quantify a risk factor for heart disease, and in particular atherosclerosis and other disorders involving cholesteryl ester deposits. The invention may also be used to determine the efficacy of treatments affecting the activity of and abnormalities in lipid transfer protein activity in physiologic samples of CETP.

In another aspect, the present invention is applied as methods of identifying a subject as having a risk factor for heart disease, atherosclerosis, coronary artery lesions, and/or disorders involving cholesteryl ester deposits by determining CETP activity in a bodily fluid from said subject. These methods are optionally practiced with reference to predetermined standard values for CETP activity in bodily fluids of subjects having these conditions. The invention also provides kits comprising components used in these methods in combination with instructions for practicing the methods.

In a further aspect, the invention provides for the use of an improved donor particle emulsion for assessing CETP activity. The improved donor particle emulsion does not contain apoA-I, which is the major protein component of high-density lipoprotein (HDL). CETP transfers cholesteryl esters from HDL to LDL or VLDL (apoB-containing lipoproteins). The invention is thus also based in part on the recognition that donor particle emulsions that are apoA-I free do not compete with endogenous HDL, which is present in a bodily fluid in varying amounts. The invention thus provides for reducing or eliminating competition from endogenous HDL, which contributes to inaccurate determinations of CETP activity in assays that use apoA-I containing donor particles. Such assays are hindered by the fact that the apoA-I containing donor particles will be of specific activities that vary depending on the amount of HDL present in a bodily fluid.

In one preferred aspect, the invention provides a method to determine CETP activity in a bodily fluid of a subject, said method comprising obtaining a sample of bodily fluid from said subject, contacting said bodily fluid with a donor and an acceptor to form a reaction mixture solution, wherein said bodily fluid comprises at least about 89% v/v of said reaction mixture solution, and detecting transfer from said donor to said acceptor to determining the CETP activity in said fluid. The donor and acceptor are preferably in solution together but may also be in separate solutions that are combined with said bodily fluid.

In another preferred aspect, the invention provides a method of determining and quantifying CETP activity in a bodily fluid comprising obtaining a sample of bodily fluid (preferably plasma) from a mammal having a source of CETP, incubating the sample, without significant dilution, in a non-radioactive CETP assay for an effective time period to obtain an incubated mixture, measuring the CETP activity of the incubated mixture to determine a CETP activity value, and comparing the sample's CETP activity value to a predetermined standard value. A non-radioactive CETP assay used in the practice of the invention preferably comprises using a prepared sonicated particle comprising a fluorescently labeled cholesteryl ester and at least one apolipoprotein to a buffer to form a buffered solution, and an emulsion of lipid added to the buffered solution to accept the transfer of labeled chloesteryl ester. After addition of the CETP containing sample to the buffered solution and passage of sufficient time, the fluoresence of the buffered solution can be measured and used as an indicator of CETP activity in the sample.

In an embodiment of the above, 50 microliters of a frozen-then-thawed human plasma sample is combined with 4 microliters of a solution containing a donor particle emulsion and acceptor as described herein. The combination is incubated for about 45 to about 90 minutes at 37° C. followed by detection of fluorescence at 535 nm with excitation at 465 nm.

In a further preferred aspect, a non-radioactive method of facilitating, simplifying and quantifying a determination of the efficacy of a compound that modulates (activates or inhibits) CETP activity, as well as a kit for carrying out the method, are provided. The method comprises obtaining a sample of bodily fluid (preferably plasma) from a mammal having a source of CETP and having been administered a CETP modulating compound, incubating the sample, without significant dilution, in a non-radioactive CETP assay for an effective time period to obtain an incubated mixture, measuring the CETP enzyme activity of the incubated mixture to determine a CETP activity value and, comparing the sample's CETP activity value to a predetermined standard value. The method and kit are used to determine the efficacy of a treatment designed to affect CETP enzyme activity. The treatment includes a compound that modulates the transcription of a gene coding for CETP, a compound that modulates the translation of a gene coding for CETP, a compound that is a treatment for atherosclerosis, a modification in diet affecting CETP activity, atherogenic diet modifications affecting CETP activity, or combinations thereof. Preferably, the compounds are inhibitors of CETP activity or expression levels in bodily fluids. Alternatively, the compounds are those used to treat heart disease, such as the statin drugs (including Mevacor® and Lipitor® and others that inhibit HMG-Coenzyme A reductase), that have been administered alone or in combination with a compound that affects CETP activity.

In other aspects, the invention provides a non-radioactive kit and method of determining an HDL/LDL risk ratio or a risk factor for obesity as well as a kit and non-radioactive method to determine the efficacy of a treatment for a medical condition associated with abnormal levels of CETP. In all of these applications, the methods of the invention are employed to obtain a value representing CETP activity in a bodily fluid sample, which value is compared to a pre-determined range. The pre-determined range may include regions of low CETP activity, moderate CETP activity, and high CETP activity which have been correlated with HDL/LDL risk ratios and/or a risk factor for obesity. Alternatively, the pre-determined range is correlated with medical conditions associated with abnormal levels of CETP, including, but not limited to, hypoalphalipoproteinemia, abnormal and normal ratios of plasma apo A-I to apo B.

MODES OF CARRYING OUT THE INVENTION

Figure 1:
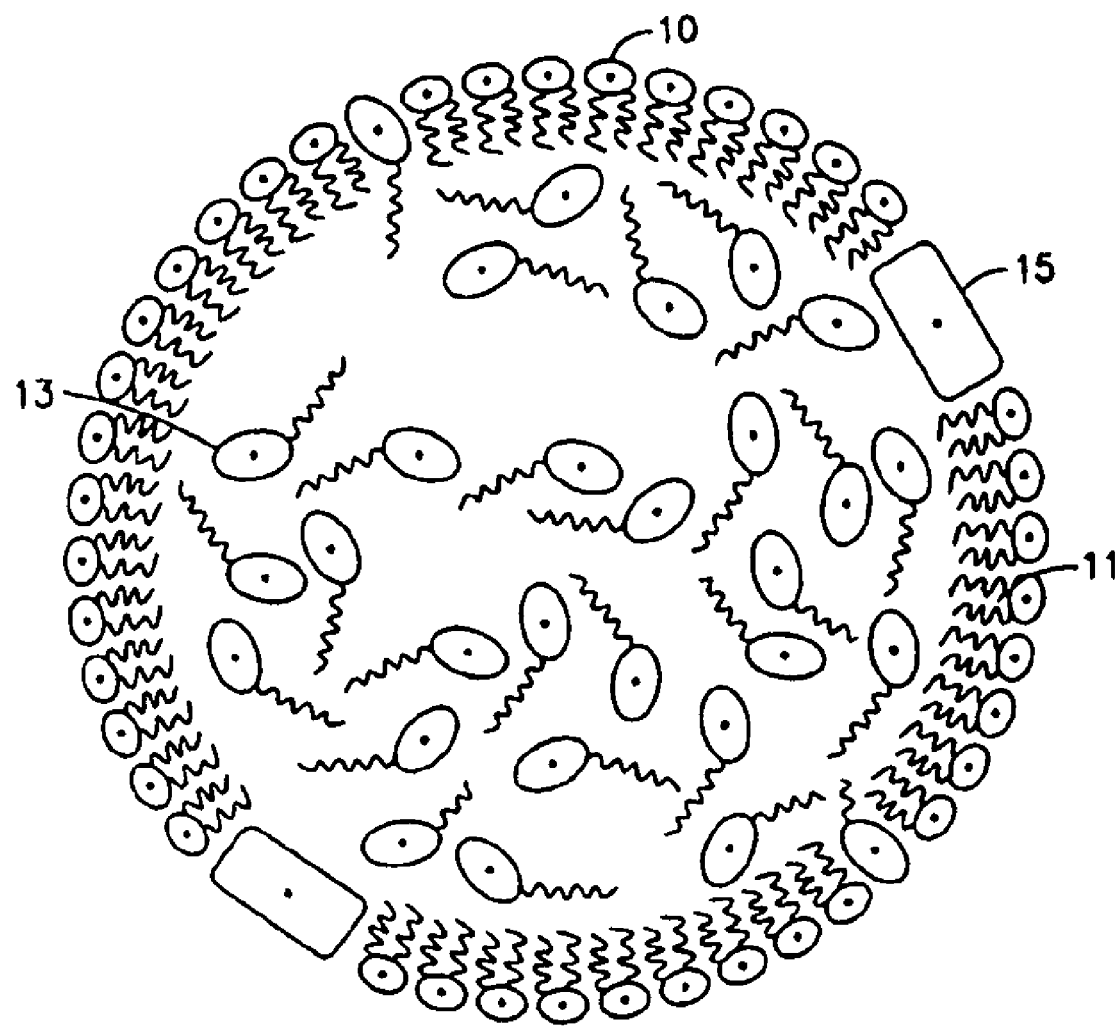
FIG. 1 is a cross section of one donor particle emulsion according to the invention.

The invention provides the ability to more accurately determine CETP activity in samples of bodily fluids from a subject. Such bodily fluid samples may be any that contains CETP activity and thus can serve as a source of CETP activity. Non-limiting examples of such bodily fluid samples include any biological fluid obtained or derived from a subject, whole blood, plasma, serum and extracts, homogenates, or secretions of liver, small intestine, spleen, adrenal gland, adipose tissue, as well as combinations of such extracts, homogenates, or secretions. Preferably, the subject is human, although other vertebrates, particularly mammals, under veterinary care may be the subjects of the present invention. Particularly preferred are animals important to drug discovery applications and animals used to model human diseases, including heart disease and atherosclerosis, that either naturally express active CETP such as but not limited to, rabbits, hamsters, hedgehogs, ducks and certain fish or transgenic animals that are modified to express CETP, such as mice.

Preferably, the bodily fluid sample is obtained from a subject that has been treated with a medication, medical protocol, dietary regimen, or physical regimen that affects CETP activity. Non-limiting examples of medications include drugs and naturally occurring compounds. The use of such samples permits the practice of the present invention to determine the efficacy and/or effect of the treatment on CETP activity in the subject. In particularly preferred embodiments of the invention, the subject has been treated by administration of a CETP activity inhibitor, and said sample contains said CETP inhibitor, or said subject has been treated by administration of an inhibitor of CETP expression at the transcriptional, translational, and/or secretion levels.

Particularly preferred in the practice of the invention is the use of samples that have been frozen to disrupt endogenous lipoproteins in the sample and reduce their effects on the assessment of CETP activity in the samples.

The samples may also be from subjects having, or suspected of having, a genetic abnormality associated with an abnormal level of CETP or CETP activity. Non-limiting examples include subjects that express abnormal levels of CETP or a CETP inhibitor. The use of such samples in combination with the present invention permits the determination of the presence of such a genetic abnormality.

In all embodiments of the invention, the level of CETP activity found in a sample of bodily fluid may be compared to the activity found in a sample from an untreated or normal subject, or a population of subjects, as reference. A diminution or enhancement of CETP mediated transfer in sample as compared to the reference identifies the sample as having an abnormal level of CETP activity which may require adjustment by use of treatments that increase or decrease CETP activity as required by the extent and type of abnormality. Preferably, the untreated subject is the same subject from whom the treated sample is obtained. The level of CETP activity may also be compared to a standard to determine the amount of activity based upon the amount of substrate transferred by CETP.

The invention also provides for the ability to more accurately assess CETP activity despite the presence of endogenous modulators (inhibitors or activators) of CETP activity. Such endogenous modulators may be naturally present and/or induced or suppressed by the treatment of a subject as described above. The endogenous modulators may also act at the level of affecting CETP expression. The effect of modulators on CETP activity may not be reflected in determinations of CETP activity in a bodily fluid sample if the sample is diluted because the modulator may be diluted beyond its ability to affect CETP activity as present in the bodily fluid. Therefore, the invention provides for the determination of CETP activity without significant dilution of a bodily fluid sample.

By significant dilution of a bodily sample, it is meant dilution of the sample by more than an equal volume of another solution. Stated differently, dilution of a sample beyond 50% v/v is significant with respect to the present invention. Therefore, the present invention provides methods that determine CETP activity in solutions, or reaction mixtures, comprising at least 50% v/v of a bodily fluid sample. More preferably, the invention is practiced with solutions comprising at least about 60%, at least about 70%, at least about 80%, at least about 85%, at least about 90%, at least about 91%, at least about 92%, at least about 93%, at least about 94%, at least about 95%, at least about 96%, at least about 97%, at least about 98%, or at least about 99% v/v of a bodily fluid sample. Of course the limitation on the maximum ratio of sample to total reaction mixture volume is the volume of the other components in the reaction volume. The other components are simply the donor and acceptor reagents as described herein, which may be formulated to be in small volumes that do not significantly dilute a bodily fluid sample upon addition thereto.

The reaction mixtures of the invention permits CETP activity to be detected. CETP ligands include two neutrally charged or non-polar lipids, namely, cholesteryl esters ("CE"), triacylglycerol, and triglycerides ("TG"). These hydrophobic, neutral lipids are present within the core of lipoprotein particles, including, but are not limited to, high density lipoproteins ("HDL"), low density lipoproteins ("LDL") and very low density lipoproteins ("VLDL"). Most lipoproteins are freely circulating in the plasma of an organism. CETP transfers the two neutral lipids CE and TG from one lipoprotein particle, the donor, to another lipoprotein molecule, the acceptor.

CETP is thus a highly specialized protein that possesses transfer activity. In some animal and human diseases, especially heritable genetic disorders, there is a deficiency in or over production of CETP that leads to a phenotypic disorder. Exemplary phenotypic disorders include extremely high levels of HDL cholesterol in animals and humans exhibiting CETP deficiency, hyperalphalipoproteinemia associated with a genetic deficiency of plasma CETP, obesity associated with high levels of CETP activity, low levels of HDL in patients exhibiting high CETP activity, null mutations of CETP associated with markedly increased levels of HDL-cholesterol, accelerated development of artheroshclerotic lesions in organisms expressing CETP genes, and hypertriglyceridemia and low HDL-C lipoprotein phenotypes associated with transgenic expression of CETP genes.

There are genetic disorders in which CETP is either totally ineffective or has an increased or decreased activity. In these genetic disorders the CETP may be affected in primary, secondary, or tertiary structure. The incorrect amino acid is the result of a gene mutation in the DNA coding for the respective enzyme, an error in transcription of the respective enzyme, or translation of the CETP protein. Genetic alterations can make CETP more efficient or less efficient. The resulting increase in efficiency of CETP may have a harmful effect on the subject animal in that increased CETP activity may lead to the conditions referred to above, and in particular is a risk factor for developing atherogenic lesions.

A non-radioactive method of simplifying the screening for defects of the gene coding for CETP affecting the activity of CETP comprises obtaining a source or sample of CETP containing bodily fluid from a subject, such as a mammal. In some embodiments of the invention, a source of CETP also includes recombinant organisms, and extracts therefrom, having a gene coding for CETP or variant thereof, incorporated into the organism's genome with expression thereof. Recombinant organisms include, by way of example, transgenic mice, and also other transgenic mammals.

The method further includes incubating for an effective time period the sample in a non-radioactive CETP assay to obtain an incubated mixture. The incubation preferably permits CETP transfer activity to transfer non-radioactively labeled neutral lipid from a donor particle to an acceptor particle. The label is preferably fluorescent and self quenching. The components used to produce the incubated mixture are preferably formulated as reagents for kits comprising instructions for the practice of the methods of the invention.

The method further includes measuring the CETP enzyme activity of the incubated mixture to determine a CETP activity value, and comparing the mixture's CETP activity value to a predetermined standard value.

A non-radioactive method of determining the efficacy, in a bodily fluid, of a compound that inhibits CETP activity is provided by the present invention. In the case of excessive activity of CETP, a compound inhibitor may be administered to a subject to inhibit CETP activity. The inhibition of CETP may occur at different levels, including, but not limited to direct inhibition of CETP activity or the inhibition of CETP expression.

Two types of CETP activity inhibitors are irreversible and reversible inhibitors. Irreversible inhibitors combine with and/or destroy the functional group of the CETP enzyme that is necessary for the enzymes' transfer activity and dissociate very slowly from the CETP enzyme. Further, there are two types of reversible inhibitors of CETP, namely, competitive and non-competitive inhibitors of these enzymes. Competitive inhibitors compete with the substrate for binding to the active site of CETP. However, once bound the competitive inhibitor cannot be transferred by CETP in the same way as a substrate can. Hence, competitive inhibition can be reversed by increasing substrate concentration. Generally, competitive inhibitors of CETP resemble the normal substrate in three-dimensional configuration. As a result of this similarity the competitive inhibitor "fools" CETP into binding to it. The effects of both irreversible and reversible inhibitors are more accurately assessed by use of the present invention because the effects of both are subject to dilution.

Organisms having increased CETP transfer activity are treated with inhibitors of CETP activity as discussed herein, changes in diet that affect CETP activity, or a combination thereof. The efficacy of these treatments on CETP activity is then evaluated using kits and methods as described herein. To accurately evaluate the effects of these treatments, the method used should not interfere with the concentration of the treatment article under test. The present invention allows CETP activity measurements to be made without significantly changing the concentration of inhibitors in a bodily fluid sample.

The method and kit of the present invention also facilitates and simplifies the determination of the efficacy of a compound that inhibits the transcription/translation of a gene coding for CETP. For example, a compound that inhibits transcription/translation of a gene coding for CETP includes a segment of DNA/RNA having a complementary sequence to the gene segment coding for the respective enzyme. Complementary sequences used as inhibitors are constructed using standard genetic engineering techniques. By way of example, a segment of "antisense" RNA is constructed or expressed to be complementary to CETP mRNA. The organism is given a treatment comprising of the complementary segment of RNA. The complementary segment of RNA base pairs with the CETP mRNA and translation of the CETP is modified. The effectiveness of such inhibitors of CETP expression is also assessed by the present invention based upon the CETP activity before and after, or in the presence and absence of, use of the inhibitor.

Constitutive enzymes are those present in organisms at more or less constant amounts, and induced enzymes vary in concentration. Induced enzymes are regulated in concentration in organisms by enzyme induction and repression. Induced enzymes are present in an organism in trace amounts but increase many (even a thousand) fold when the enzyme's substrate is detected by the organism. An agent capable of inducing the synthesis of an enzyme is an inducing agent. CETP is an enzyme whose gene is subject to dietary regulation and diet induced changes in lipid metabolism. Atherogenic diets, e.g. those high in cholesterol, are capable of inducing the synthesis of CETP and increasing the risk associated with the formation of artherosclerotic lesions.

A dietary modification regimen is prescribed by a healthcare professional including a doctor, nurse, dietician and the like that directly affects the induction, activity, or combination thereof, of CETP. The dietary modification regimen is used as a treatment to directly or indirectly affect the level of CETP activity. Prior to the dietary modification regimen, a baseline CETP value is determined for a patient using the method and kit described herein. The baseline CETP value is compared to a pre-determined range of values considered normal for the patient's phenotype, age, gender, and/or genotype. Where the patient's CETP value is outside the norm, a treatment affecting CETP activity is recommended. The treatment may be a dietary modification regimen, administration of a compound that inhibits CETP, administration of a compound that affects the transcription/translation of CETP, or combinations of these treatments.

In the case of a dietary modification regimen, the patient follows the regimen over a predetermined period of time. The treatment affects the induction of CETP. Where the treatment comprises a non-atherogenic diet regimen and/or physical exercise, CETP activity in bodily fluids are expected to decrease, and there is a decreased risk factor for developing atherosclerosis. After or during treatment, a sample of the patient's bodily fluid may be obtained and tested in accordance with the present invention to assess CETP activity and determine a new value for the activity. Further treatment may be prescribed to further affect CETP activity as needed.

In contradistinction to CETP induction, there is CETP enzyme repression. Enzyme repression involves the "turning off" of the synthesis of the CETP enzyme upon the addition of a compound or upon treatment of a patient with the compound. The CETP repression concept is central to the principle of cell economy in that once high levels of CETP enzyme are no longer needed in an organism, the respective enzymes are no longer made.

CETP enzyme regulation is in the form of transcriptional control, translational control, and control of secretion or export into the extracellular environment. Transcriptional control relates to the control of the initiation and/or rate of transcription of the genes coding for CETP into their corresponding mRNAs. Translational control involves the control of the initiation and/or rate of synthesis of the CETP polypeptide chain from its respective mRNA template. There are regulatory genes coding for regulatory proteins of CETP called CETP repressors. The CETP repressor binds to the DNA segment coding for CETP called the CETP operator. Further, a CETP inducer can bind to a CETP repressor to release the CETP repressor from the DNA binding site. The methods and kits described herein are used to measure the efficacy of CETP repressors, CETP inducers, compounds affecting the transcription of CETP, compounds affecting the translation of CETP, and compounds affecting the secretion or export of CETP.

As with CETP induction, the application of the assay method during a course of treating a subject via CETP repression can be evaluated by the ability of the treatment to control the levels and/or activity of CETP in the subject. The treatment may be modified to increase or decrease the level of repression based upon the level of CETP activity as determined by use of the present invention.

DONOR AND ACCEPTOR PARTICLE

As used herein, a "donor" particle refers to the particle responsible for donating cholesteryl ester or other neutral lipid to CETP for transfer. An "acceptor" particle refers to the particle in an activity measurement system (assay) responsible for accepting cholesteryl ester or other neutral lipid transferred by CETP. Stated differently, a cholesteryl ester or other neutral lipid substrate to be transferred by CETP is resident in a donor particle, while an acceptor is the destination to which the substrate is transferred.

Preferred substrates for use in the present invention are cholesteryl esters ("CE") and triglycerides ("TG"). Other potential substrates may be tested in the assay of the invention to ascertain their ability to be transferred by CETP. The substrates are preferably labeled in a manner that permits the detection of their transfer from a donor to an acceptor. Preferred labels are those that are detectable upon transfer away from a donor particle, such as self-quenching labels that exhibit enhanced fluorescence once they have been transferred away from a concentrated label environment, such as that of a donor particle. Such labels are particular preferred in the case of homogenous assay formats where donor and acceptor are not separated from each other. Non-limiting examples of such fluorescent labels include 5-butyl-4,4-difluoro-4-bora-3a,4a-diaza-s-indacen (BODIPY® from Molecular Probes, Inc. of Eugene, Oreg.), fluorescein, dansyl, rhodamine, or N-(7-nitrobenz-2-oxa-1,3-diazol-4-yl)amino (NBD) which can be readily coupled to CETP substrates.

If the assay is performed in a heterogeneous format, virtually any label can be used because the acceptor and donor particle will ultimately be separated. For example, the acceptor itself might be coupled to a member of a specific binding pair such as an antibody or fragment thereof or biotin and removed from the reaction mixture at various times and the level of label assessed. Thus, in this instance, the substrate may be labeled with a radioisotope, a fluorescent moiety, an enzyme (which then can be assayed using standard enzyme-based assays) or any other suitable label known in the art.

The donor particle is preferably an emulsion obtained by use of a suitable phospholipid emulsifier. Non-limiting examples include phosphatidylcholine and phosphatide extract. The substrate to be transfer may be dispersed throughout the emulsion or be concentrated within a portion of the emulsion. The emulsions may, of course, comprise other components, but such components are preferably not substrates for CETP transfer activity. The ratio of the components to a substrate may be found by routine optimization. In particularly preferred embodiments of the invention, the donor emulsion is as disclosed herein and does not contain apoA-I protein.

The acceptor is typically an emulsion comprising lipoprotein particles. Non-limiting examples include Intralipid™ and acceptors prepared from fresh human plasma. Other examples of donors and acceptors are provided in U.S. Pat. Nos. 5,770,355; 5,618,683; 5,585,235 and 6,174,693. The ratio of acceptor to donor is kept appropriately high such that intra-donor particle transfer is not appreciable.

The donor and acceptor emulsions may be maintained in buffered solutions for a time prior to use in the detection of CETP activity. The detection of activity may be made after sufficient time has elapsed after combination of donor, acceptor, and the CETP activity of a bodily fluid sample to effect transfer, typically about 5 or 15 to about 90 minutes, preferably about 45 to about 90 minutes, at about 37° C. The transfer can be monitored by the transfer of label as described above at various times after combination and mixing. The signal is monitored in a manner appropriate to the choice of label; in a preferred embodiment, the enhancement of fluorescence of a self-quenched label is measured in a homogeneous assay.

Method 1 to Prepare Donor

A self-quenching fluorescent neutral lipid, such as cholesteryl linoleate or other cholesteryl ester labeled with N-(7-nitrobenz-2-oxa-1,3-diazol-4-yl)amino (NBD) to yield a molecule NBD-CE, is emulsified by a suitable emulsifier such as phospholipid, like phosphatidylcholine (PC). Although the term emulsify is exemplified by a specific technique below, the present invention is concerned with incorporating the NBD lipid into an emulsified particle efficiently so as to achieve self-quenching emission characteristics of the label. There are many techniques known to emulsify hydrophobic or non-water soluble compounds, such as, NBD-CE or NBD-triglyceride (NBD-TG), and many compounds that will act as emulsifying agents.

Referring to FIG. 1, the emulsion 10 is prepared by sonicating 20 micromoles of N-(7-nitrobenz-2-oxa-1,3-diazol-4-yl)amino (NBD) labeled neutral lipid (CE or TG) 13, with 13 mg of phospholipid (PL) 11, at a power output just under that which causes the sonic probe to cavitate within the sample. A temperature above the melting point of the mixture of component lipids is maintained for 45 minutes in a buffer of 10 ml, 0.1M KCl/10 mM trizma-HCl, pH=8. The sonicated mixture is rapidly cooled to a temperature of 40 degrees Celsius. Ten (10) mg of apolipoprotein apoA-I 15 in 2.5 molar urea is added in less than 1 ml over 15 min. at a sonication power half of that used for the high temperature sonication.

For applications of the present invention requiring a particle similar to HDL, the resulting emulsion is ultracentrifuged at a density of 1.063 g/ml with 1.21 g/ml underlay and a 1.006 g/ml overlay. The HDL density class particle may be harvested from the 1.063 g/ml middle zone. This particle utilizes apolipoprotein apoA-I for stabilization, similar to physiological conditions. Stabilization of the fluorescent donor particle may also be accomplished with synthetic, amino acid peptides or casein.

Method 2 to Prepare Donor

Figure 2:
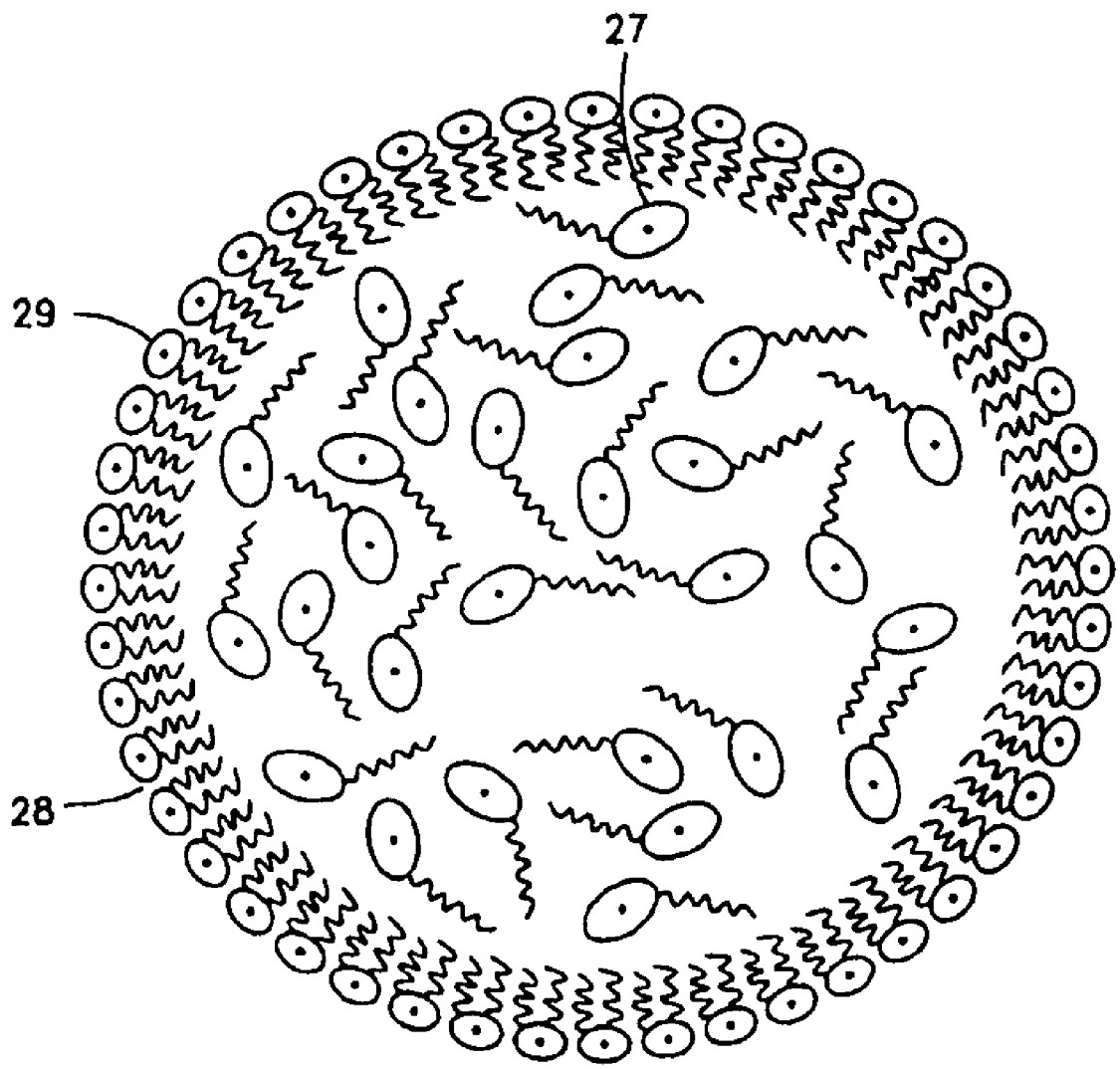
FIG. 2 is a cross section of a preferred donor particle emulsion according to the invention.

FIG. 2 shows the particle 28 produced by a second method of fluorescent neutral lipid donor synthesis. In this method, the emulsifier (PC) of Method 1 is replaced by phosphatide (PL) 29 extract. The phosphatide extract is derived from egg yolk or soybean, and includes all phospholipids associated with each source, in particular: lecithin>60%, phosphatidyl-ethanolamine>15%, lysolecithin<4%. The extract stabilizes the emulsion by providing charged emulsifying phospholipids 29. The charged phospholipids emulsify the fluorescent core comprised of NBD-CE 27, producing a net charge associated with each particle. The net charge associated with each particle causes repulsion between the fluorescent donor particles thereby preventing fusion of the particles over time. The apolipoprotein apoA-I of the previous method of donor particle synthesis is eliminated by use of the PL extract. The sonication is performed at 63 degrees centigrade (C.) to 68 degrees C.

FIG. 2 illustrates a synthetic or synthesized donor particle representative of an emulsion. The NBD-labeled neutral NBD-CE 27 contained within the core of the synthetic particle will not yield substantial fluorescent emission intensity when illuminated with excitation wavelength. Instead, the energy of the excited state is dissipated in radiationless energy transitions upon collision with other NBD-CE molecules. The non-fluorescent loss of energy is dependent upon molecular interactions associated with the core sequestered NBD-neutral lipid.

The monolayer of PL molecules 29 of FIG. 2, in the synthetic particle is comprised of a polar head group and non-polar hydrophobic tail. The conditions under which the emulsification process is performed enables the non-polar or hydrophobic tail of the PC molecule to partition with the hydrophobic NBD-neutral lipid, NBD-CE 27 of FIG. 2. The partitioning of hydrophobic constituents of the co-sonication mixture traps the NBD-neutral lipid into a small area relative to the area of the aqueous phase. The PC emulsified NBD-neutral lipid components are in stable non-aqueous or hydrophobic environment at high concentration with respect to collisional proximity and accordingly yield little fluorescence intensity.

Method to Prepare Acceptor

Fresh human plasma has an initial density of 1.006 gm/ml. Apo-B containing lipoproteins comprised of low density lipoprotein and very low density lipoprotein are excellent acceptor substrates for CETP. Therefore, according to the invention, to fresh human plasma is added solid sodium bromide (NaBr) to adjust the density of the plasma from 1.006 to 1.063 gm/ml (72.4 gms of NaBr to 940 mls of plasma). The plasma is ultracentrifuged at 1.063 gm/ml in a Beckman 50.2 rotor at 40,000 rpm for 48 hours.

Figure 3:
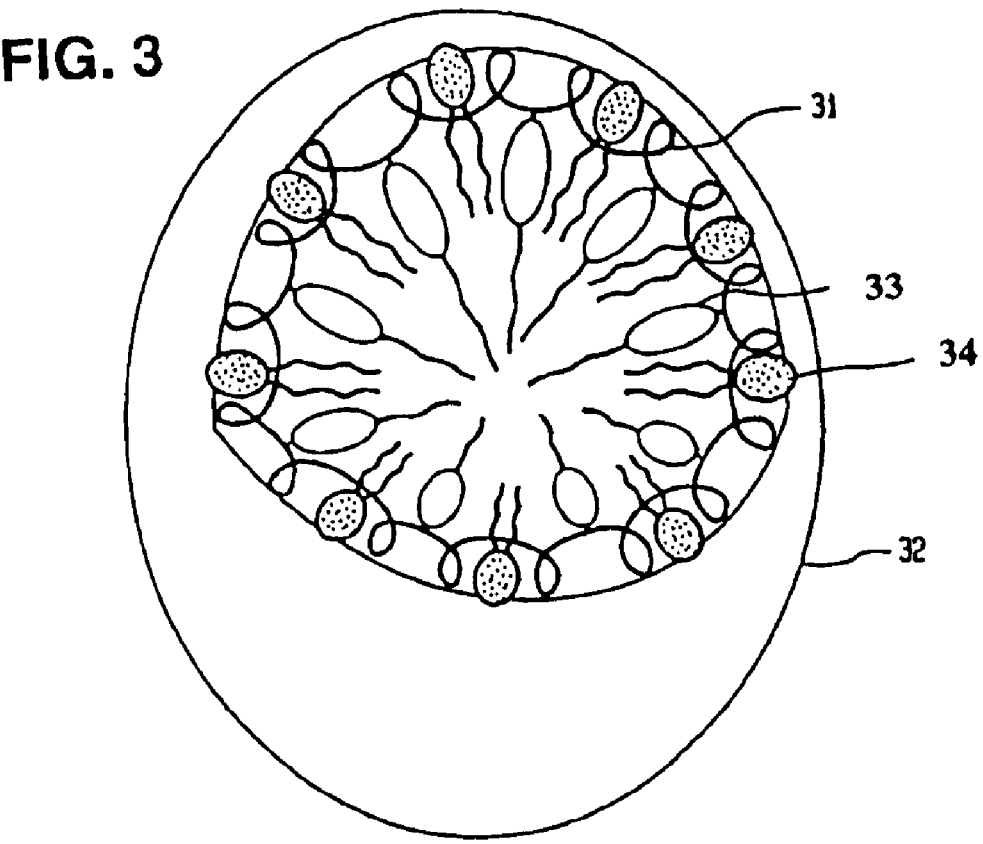
FIG. 3 is a cut away view of an acceptor lipoprotein used in the invention.
Figure 4:
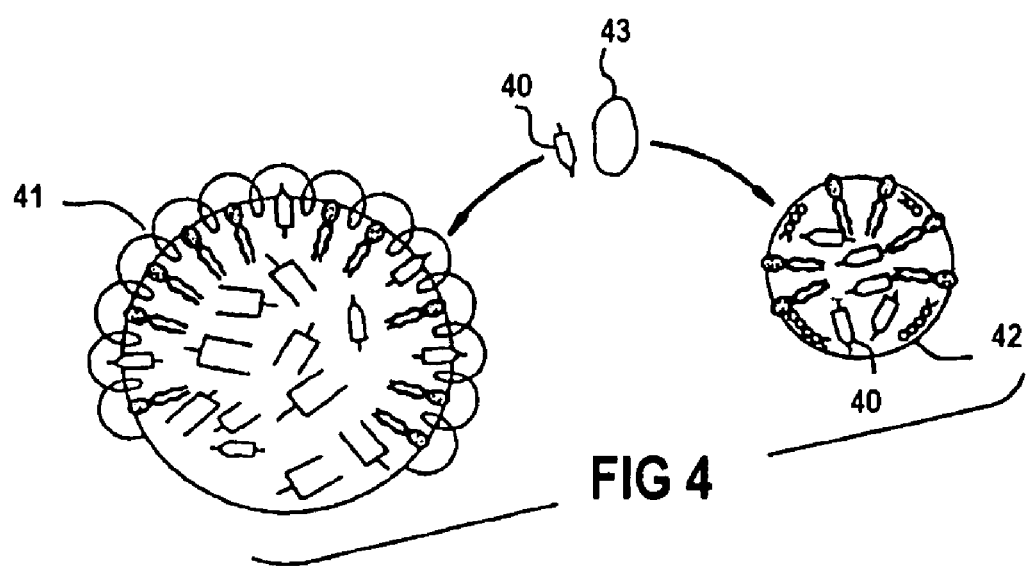
FIG. 4 is a schematic illustration of the CETP transfer activity assay of the invention.

After ultracentrifugation, a turbid top layer, clear middle layer and turbid bottom layer will result. The top layer is the density less than 1.063 gm/ml layer while the turbid bottom layer is the density greater than 1.063 gm/ml layer. The top layer is removed and contains all the apolipoprotein B containing particles from the plasma. These particles are relatively large spherical particles rich in neutral lipids such as triglycerides (TG) which provide an available substrate for CETP to hetero-exchange TG from acceptor for substrate (such as NBD-CE or BODIPY®-CE) from a donor. FIG. 3 illustrates the type of particles associated with the density less than 1.063 gm/ml top layer. The apo-B containing particle 32 includes apo proteins 31, neutral lipids 33, such as TG's and CE's and an outer layer comprised of phospholipids 34. This fraction of particles is preferably used as the acceptor in the present invention and normalizes any differences in acceptor concentration in the plasma samples to be measured. A donor particle without apoA-I is preferred because it will not compete with endogenous apoA-I containing lipoproteins which would alter the specific activity of the donor.

While the above has been described with respect to human plasma, lipoprotein containing plasma from other animals may also be used to prepare acceptors for use in the present invention by routine methods.

Other Acceptors

In some embodiments, such as when fresh plasma is used by the invention as a CETP containing sample, it may be preferable to utilize the endogenous lipoproteins present in the plasma sample as acceptor. Therefore, a single bodily fluid sample from a subject can be used both to provide the CETP activity to be assayed as well as the source of acceptor for accepting transfer of substrate from a donor. This embodiment of the invention advantageously provides the ability to obviate the need to supply exogenous acceptor. The embodiment is preferably practiced with donor comprising a labeled substrate that permits detection of CETP activity based upon transfer of substrate away from the donor regardless of the nature of the acceptor.

Alternatively, a bodily fluid sample from a subject can be used to provide one portion of the sample for processing as described above to prepare acceptor. Another portion of the sample can be used as the CETP containing sample to be tested. However, the presence of apo-B containing lipoproteins in the CETP containing sample may introduce inaccuracies into the methods of the present invention because these lipoproteins may also act as acceptors. Therefore, the invention also provides for the optional disruption of endogenous lipoprotein particles in CETP containing samples. Such samples may be frozen, optionally at −40 or −80° C., to disrupt the integrity of endogenous lipoprotein particles. Freezing lipoproteins will decrease their importance as a substrate to CETP. Freezing of the samples will also allow long term storage of the samples without a loss of CETP activity or decomposition of inhibitor(s) present in the sample.

Such frozen samples may be thawed and combined with the density less than 1.063 gm/ml fraction of plasma as prepared above to normalize the acceptor population among the samples. Further, donor particle without ApoA-I is used as the preferred substrate containing donor for assessing CETP transfer activity. CETP prefers a donor emulsion without apoA-I over endogenous HDL or frozen-then-thawed HDL.

Kits

The components useful in the invention can be provided in the form of a kit which contains at least a container which provides labeled donor particles, preferably as an emulsion, and instructions or label indications for its use in the methods of the invention. The kit optionally further contains a container which contains an acceptor, preferably prepared from plasma as described above. If desired, only the container of labeled donor may be provided, along with instructions for the preparation of an acceptor emulsion or for the use of lipoproteins present in a CETP containing sample as acceptor.

Applications

The assay of the present invention may be used to assess a medical condition related to CETP activity. These conditions include but are not limited to heart disease and atherosclerosis, hypoalphalipoproteinemia, abnormal ratios of plasma apo A-I to apo B, increased secretion and levels of ApoB-containing lipoproteins, coronary artery lesions, diabetes, obesity, and disorders involving cholesteryl ester deposits and transfer.

The invention may be used to screen CETP activity in plasma from mammals, including humans, that have been treated with an inhibitor of CETP activity or measure the effects of an endogenous inhibitor of CETP activity. The invention allows CETP activity to be determined on a bodily fluid sample derived from a test subject without dilution of the sample which would change the concentration of inhibitor present in the sample. A variety of fluids may be used, depending on the interest of the skilled person and the presence of CETP activity. Exemplary CETP inhibitors include the following compounds: a) 7[4'-trifluoromethyl-biphenyl-2-carbonyl)amino]-quinoline-3-carboxylic acid amides; b) Oxy substituted 4-carboxyamino-2-methyl-1,2,3,4-tetrahydroquinolines; c) 4-carboxyamino-2-substituted-1,2,3,4-tetrahydroquinoline; d) Substituted biphenyls; e) pyridines; and f) tetrahydroquinolines.

The following is put forth so as to provide those of ordinary skill in the art with a complete disclosure and description of how to make and use the present invention, and are not intended to limit the scope of what is regarded as the invention nor are they intended to represent that the experiments below are all or only experiments performed. Efforts have been made to ensure accuracy with respect to numbers used (e.g. amounts, temperature, etc.) but some experimental errors and deviations should be accounted for. Unless indicated otherwise, temperature is in degrees Celsius, and pressure is at or near atmospheric.

EXAMPLE 1

Determination of CETP Activity

A method for CETP activity measurement according to the present invention comprises: 1) mixing 7 µl of a donor particle emulsion with 30 µl of isolated human plasma at density less than 1.063 gm/ml as the acceptor; 2) incubating 4 µl of the mixture of 1) with 50 µl of a previously frozen-then-thawed plasma sample to be tested for CETP activity for 45 to 90 minutes at 37 degrees Celsius; and 3) measuring the fluorescent emission intensity of the mixture from 2). The percentage of plasma is about 93% v/v in the mixture.

Alternative exemplary amounts include donor emulsion containing approximately $1.9 \times 10^{-10}$ moles of NBD-labeled neutral lipid mixed with 10 to 30 microliters of acceptor (density<1.063 gm/ml plasma fraction) and using 4 microliters of this mixture to 50 microliters of frozen-then-thawed plasma sample to be tested and the fluorescence at 538 nanometers (nm) is read at an excitation wavelength of 465 nm in a standard laboratory plate reading fluorimeter.

Figure 5:
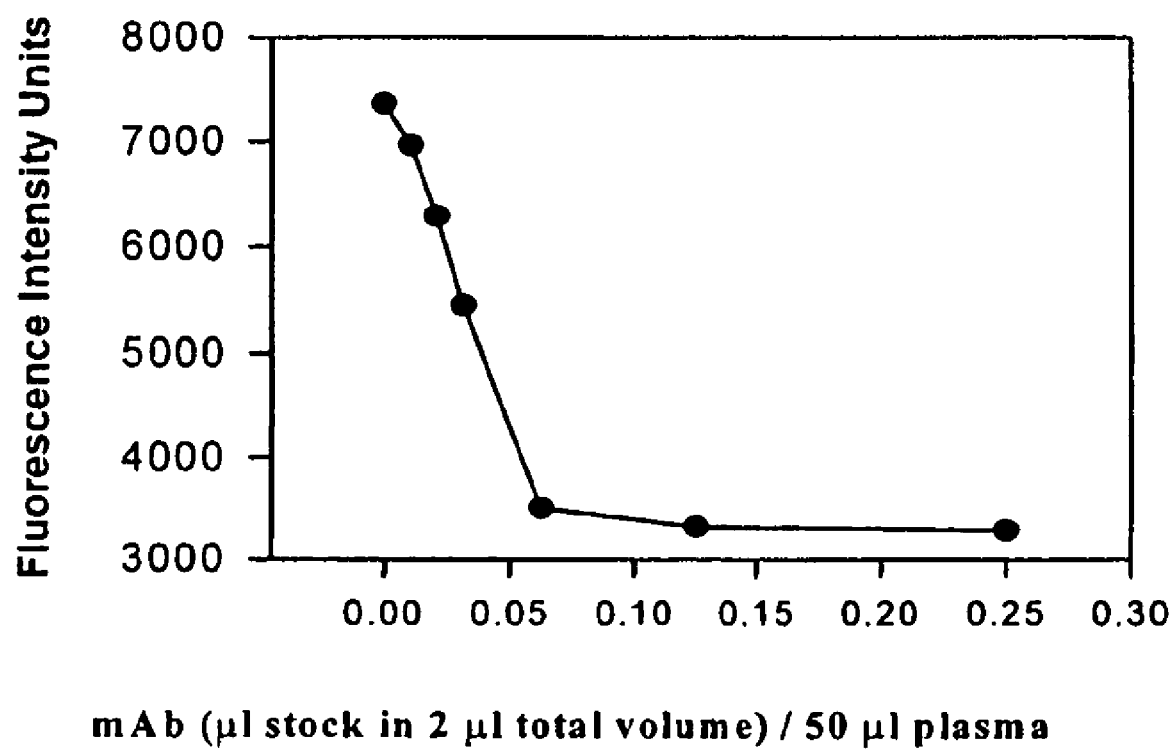
FIG. 5 is a graph of CETP activity in plasma as affected by pre-treatment with a CETP inhibitory monoclonal antibody.

Referring to FIG. 5, the experiment was performed with 50 µl samples of frozen-then-thawed human plasma that were pre-treated with a CETP inhibitory monoclonal antibody. The antibody pre-treatments were dilutions of stock mAb in 2 µl total Ab volume added to each 50 µl plasma sample. Following the pre-treatments, the plasma samples were placed in a microplate and 4 µl reagent according to the invention was added. The samples were incubated for 90 minutes at 37° C. The assays were read at an excitation wavelength of 465 nm and emission wavelength 535 nm. The total assay volume was 56 µl. The percentage of pre-treated plasma is about 89% v/v in the mixture.

All references cited herein, including patents, patent applications, and publications, are hereby incorporated by reference in their entireties, whether previously specifically incorporated or not.

Having now fully described this invention, it will be appreciated by those skilled in the art that the same can be performed within a wide range of equivalent parameters, concentrations, and conditions without departing from the spirit and scope of the invention and without undue experimentation. The invention also includes all of the steps, features, compositions and compounds referred to or indicated in this specification (unless specifically excluded) individually, collectively, and any and all combinations of any two or more of said steps or features.

The invention claimed is:

1. A method to determine cholesteryl ester transfer protein (CETP) activity in a bodily fluid of a subject, which method comprises:
obtaining a sample of bodily fluid from said subject;
contacting said sample of bodily fluid with a donor, wherein said donor does not comprise apoA-I, comprising a labeled CETP substrate, and an acceptor, to which said substrate will be transferred by any CETP activity, to form a reaction mixture solution, wherein at least about 89% v/v of said reaction mixture solution is said sample of bodily fluid;
and detecting transfer of said substrate from said donor to said acceptor to determine the activity of CETP in said fluid;
wherein said sample contains an endogenous CETP inhibitor or activator.

2. The method of claim 1 wherein said substrate is labeled with a self quenching fluorescent molecule.

3. The method of claim 2 wherein said self-quenching fluorescent molecule is N-(7-nitrobenz-2-oxa-1,3-diazol-4-yl)amino (NBD), 5-butyl-4,4-difluoro-4-bora-3a,4a-diaza-s-indacene, fluorescein, dansyl, or rhodamine.

4. The method of claim 3 wherein said molecule is NBD.

5. The method of claim 3 wherein the CETP substrate is a cholesteryl ester, a triacylglycerol, or a triglyceride.

6. The method of claim 5 wherein said substrate is cholesteryl linoleate.

7. The method of claim 1 wherein said acceptor is an apo-B containing lipoprotein.

8. The method of claim 1 wherein said sample has been frozen.

9. The method of claim 1, further comprising computing, from a standard, the amount of substrate transferred.

10. The method of claim 1, wherein said determining of the amount of label incorporated into the acceptor is performed on the reaction mixture without separating the acceptor from said reaction mixture.

11. The method of claim 1, further comprising comparing the level of CETP activity to a pre-determined standard value indicating the presence of a risk factor for heart disease, atherosclerosis, hypoalphalipoproteinemia, abnormal ratios of plasma apo A-I to apo B, increased levels of ApoB-containing lipoproteins, coronary artery lesions, diabetes, and/or obesity.

12. The method of claim 1, further comprising comparing the level of CETP activity to a pre-determined standard value indicating the presence of a genetic defect in the gene encoding CETP that affects the amount or activity of CETP protein in said sample.

13. The method of claim 1 wherein said subject has been treated by administration of a CETP activity inhibitor, and said bodily fluid contains said CETP inhibitor, and/or has been treated with a non-atherogenic diet modification regimen that affects physiological CETP activity.

14. The method of claim 13 wherein said inhibitor inhibits cholesterol synthesis and/or transfer, inhibits CETP expression, or is used to treat atherosclerosis.

15. The method of claim 14 wherein said inhibition of CETP expression is by inhibiting the transcription or translation of CETP.

16. A method to determine cholesteryl ester transfer protein (CETP) activity in a bodily fluid of a subject, which method comprises:
obtaining a sample of bodily fluid from said subject, wherein said fluid contains apo-B containing lipoproteins;
contacting said sample of bodily fluid with a donor, wherein said donor does not comprise apoA-I, comprising a labeled CETP substrate which will be transferred to said lipoproteins by any CETP activity, to form a reaction mixture solution, wherein at least about 89% v/v of said reaction mixture solution is said sample of bodily fluid;
and detecting transfer of said substrate from said donor to said lipoproteins to determine the activity of CETP in said fluid;
wherein said sample contains an endogenous CETP inhibitor or activator.

\* \* \* \* \*